(12) United States Patent
Williams et al.

(10) Patent No.: US 6,657,022 B2
(45) Date of Patent: Dec. 2, 2003

(54) INHIBITING CATALYST COKE FORMATION IN THE MANUFACTURE OF AN OLEFIN

(75) Inventors: Bryce A. Williams, Evanston, IL (US); Stephen N. Vaughn, Kingwood, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 10/170,065

(22) Filed: Jun. 11, 2002

(65) Prior Publication Data

US 2003/0055183 A1 Mar. 20, 2003

Related U.S. Application Data

(60) Provisional application No. 60/302,462, filed on Jul. 2, 2001.

(51) Int. Cl.[7] .................................................. C08F 2/34
(52) U.S. Cl. ..................... 526/72; 526/351; 526/352; 585/638; 585/639; 585/640
(58) Field of Search .................. 526/72, 351, 352; 585/638, 639, 640

(56) References Cited

U.S. PATENT DOCUMENTS

| | | | |
|---|---|---|---|
| 6,023,005 A | 2/2000 | Lattner et al. | 585/639 |
| 6,166,282 A * | 12/2000 | Miller | 585/638 |

\* cited by examiner

*Primary Examiner*—David W. Wu
*Assistant Examiner*—William Cheung
(74) *Attorney, Agent, or Firm*—Paul T. Lavoie

(57) ABSTRACT

Disclosed is a method for inhibiting catalyst coke formation in the manufacture of an olefin. In particular, the method inhibits coke formation on a silicoaluminophosphate molecular sieve catalyst in the manufacture of ethylene and/or propylene. The method includes contacting an oxygenate-containing feedstock with a silicoaluminophosphate molecular sieve catalyst to form the olefin-containing product, and separating the olefin-containing product from the catalyst. An unregenerated portion of the separated catalyst is cooled before contacting with additional oxygenate feedstock to reduce coke formation on the catalyst.

48 Claims, 2 Drawing Sheets

INHIBITING CATALYST COKE FORMATION IN THE MANUFACTURE OF AN OLEFIN

This application claims priority to U.S. Ser. No. 60/302,462, filed Jul. 2, 2001, which is fully incorporated herein by reference.

FIELD OF THE INVENTION

This invention relates to inhibiting catalyst coke formation in the manufacture of an olefin. In particular, this invention relates to inhibiting coke formation on a silicoaluminophosphate molecular sieve catalyst in the manufacture of ethylene and/or propylene.

BACKGROUND OF THE INVENTION

Demand for polyolefins, e.g., polyethylene and polypropylene, has been steadily increasing. It is projected that the increased demand for polyolefins will outpace the availability of raw materials, e.g., ethylene and propylene, from which polyolefins can be made.

Olefins which are used to make polyolefins have been traditionally produced from petroleum feedstock by either catalytic or steam cracking of the petroleum. The cost of petroleum cracking has steadily increased, however, making it important to find alternative feedstock sources for olefins.

Oxygenates are a promising alternative feedstock for making olefins. Particularly promising oxygenate feedstock are alcohols, such as methanol and ethanol, dimethyl ether, methyl ethyl ether, diethyl ether, dimethyl carbonate, and methyl formate. Many of these oxygenates can be produced by fermentation, or from synthesis gas derived from natural gas, petroleum liquids, carbonaceous materials such as coal, recycled plastics, municipal wastes, or any appropriate organic material. Because of the wide variety of sources, oxygenates have promise as an economical source for olefin production.

One way in which olefins can be made from the alternative oxygenate feedstock is by catalytic conversion. In U.S. Pat. No. 4,499,327, for example, a catalytic process for converting methanol to olefins is described. The catalyst used in that process contains a silicoaluminophosphate molecular sieve.

Of course, it is highly desirable to convert as much of the oxygenate feedstock as possible into as much olefin product as possible. Various methods of doing such have been suggested. For example, U.S. Pat. No. 4,677,242 describes a method of increasing the amount of ethylene and propylene produced from the catalytic conversion of methanol by adding an aromatic diluent to the methanol. The catalyst that is used in the process contains a silicoaluminophosphate molecular sieve. The use of the diluent is considered to result in an increased amount of ethylene product.

U.S. Pat. No. 4,499,314 also discloses a catalytic process for converting methanol to ethylene and para-xylene. The catalyst that is used is ZSM-5. Promoters are used to promote either the formation of aromatics products or olefins products. Benzene, toluene and para-xylene are preferred aromatics promoters. Ethylene, propylene and butenes are preferred olefin promoters.

Song et al., "Supramolecular Origins of Product Selectivity for Methanol-to Olefin Catalysis on HSAPO-34," *J. Am. Chem. Soc.,* 2001, 123, pp. 4749–4754, indicate that ethylene selectivity in methanol-to-olefin (MTO) catalysis is related to the number of methyl groups on benzene rings trapped in the cages of a preferred HSAPO-34 catalyst. Co-feeding water with methanol was found to significantly increase the average number of methyl groups per ring, and increase ethylene selectivity.

U.S. Pat. No. 6,166,282, discloses an MTO process which uses a fast-fluidized bed reactor. The process is carried out in a reaction zone having a dense phase zone in the lower reaction zone and a transition zone which extends into a catalyst disengaging zone. A portion of the catalyst is circulated from the disengaging zone to the lower, dense phase zone. The arrangement is considered to enable reduction in catalyst inventory.

There remains, nevertheless, a desire to improve the economic attractiveness of the oxygenate conversion process. Catalysts and methods to produce olefins from oxygenates are needed which increase the selectivity of the oxygenate conversion reaction, particularly to ethylene and propylene, without resorting to adding costly product enhancing promoters.

SUMMARY OF THE INVENTION

In order to overcome the various problems associated with providing large quantities of olefin product which can ultimately be used in the manufacture of polyolefin compositions, this invention provides a method of inhibiting catalyst coke formation during the conversion of an oxygenate feedstock to an olefin-containing product. In a preferred embodiment, the oxygenate feedstock is reacted with a silicoaluminophosphate molecular sieve catalyst at an average reactor temperature effective to form the olefin-containing product. The olefin-containing product is then separated from the catalyst and at least a portion of the catalyst is cooled to a temperature below the average reactor temperature. The cooled portion of the catalyst is then contacted with oxygenate-containing feedstock without first regenerating the catalyst.

It is preferred that the average reactor temperature of this method is from of about 350° C. to about 525° C. and the cooled portion of the catalyst is from about 10° C. to about 30° C. cooler than to average reactor temperature. Further, the average coke content of regenerated catalyst is less than about 2%, by weight, and the average coke content of the combination of separated and regenerated catalyst is from about 2%, by weight, to about 30%, by weight.

In another embodiment of the invention, a portion of the separated catalyst is regenerated and combined with the cooled portion of the catalyst prior to contacting the cooled portion of the catalyst with additional oxygenate-containing feedstock. Alternatively, a portion of the separated catalyst is regenerated and combined with the cooled portion of the catalyst after contacting the cooled portion of the catalyst with additional oxygenate-containing feedstock.

The invention further provides a method in which the olefin-containing product is separated from the catalyst and collected. The recovered olefin-containing product may contain at least about 85%, by weight, of ethylene, propylene, or mixtures thereof.

The invention further provides a method in which the oxygenate-containing feedstock may be selected from methanol, ethanol, n-propanol, isopropanol, C4–C20 alcohols, methyl ethyl ether, dimethyl ether, diethyl ether, di-isopropyl ether, formaldehyde, dimethyl carbonate, dimethyl ketone, acetic acid, and mixtures thereof.

The invention further provides that the molecular sieve catalyst is a silicoaluminophosphate molecular sieve selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, mixtures thereof, and intergrowths thereof. The molecular sieve catalyst may be contacted with the oxygenate-containing feedstock at a temperature of from about 200° C. to about 700° C. In one embodiment, the molecular sieve catalyst is contacted with the oxygenate-containing feedstock at a gas superficial velocity of at least about 1.0 meters per second, and preferably at least about 2.0 meters per second.

In another embodiment, the invention provides polypropylene and/or polyethylene manufactured according to the method of the present invention.

The present invention will be better understood by reference to the Detailed Description of the Invention when taken together with the attached drawings.

DETAILED DESCRIPTION OF THE INVENTION

Figure 1:
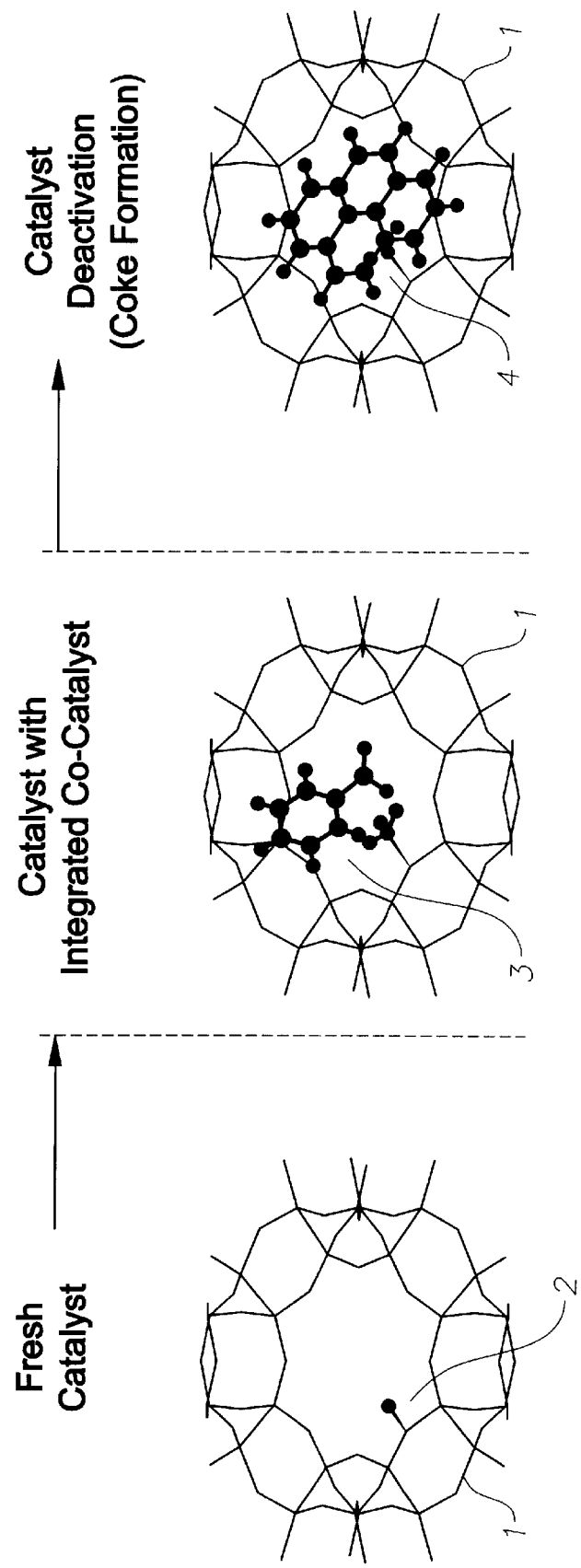
FIG. 1 is an illustrative representation of the formation of co-catalyst with a small pore molecular sieve.

The present invention provides a method of inhibiting catalyst coke formation during the conversion of an oxygenate feedstock to an olefin-containing product. In a preferred embodiment, the oxygenate feedstock is reacted with a silicoaluminophosphate (SAPO) molecular sieve catalyst at an average reactor temperature effective to form the olefin-containing product. The olefin-containing product is then separated from the catalyst and at least a portion of the catalyst is cooled to a temperature below the average reactor temperature. The cooled portion of the catalyst is then contacted with oxygenate-containing feedstock without first regenerating the catalyst. Additionally, selectivity of converting feedstock to product is in favor of prime olefins (ethylene and propylene).

The SAPO molecular sieve catalysts serve as particularly desirable catalytic materials in converting oxygenate feedstock to olefin compositions. They are particularly good catalysts for making olefins such as ethylene and propylene from oxygenate compounds.

According to this invention, significant quantities of ethylene and propylene can be produced from oxygenate feedstock using catalysts containing SAPO molecular sieves if hydrocarbon material is introduced or produced from an oxygenated feedstock into the porous framework of the silicoaluminophosphate molecular sieves under the appropriate conditions, then contacted with feedstock. Once the silicoaluminophosphate molecular sieve contains a measurable quantity of a catalytically active integrated hydrocarbon co-catalyst, which may be at least one single ring aromatic compound, oxygenate contacting the silicoaluminophosphate molecular sieve at appropriate reaction conditions will be converted to form a product that has a substantial quantity of ethylene and propylene relative to what has been previously achievable.

It is particularly desirable in this invention to maintain a relatively high gas superficial velocity in the reaction zone to more approximate ideal plug flow behavior. In this invention, ideal plug flow occurs when the reactants and products move homogeneously through the reaction zone as plugs moving parallel to a longitudinal axis in the reaction zone. For purposes of this invention, the reaction zone begins at the initial point of contact of feed with catalyst (whether fresh catalyst, recirculated catalyst, regenerated catalyst or a mixture thereof), and continues to the point of disengagement of product from catalyst (e.g., cyclone or other type separator). Also for purposes of this invention, the term, "gas superficial velocity," or GSV, is defined as the combined volumetric flow rate of vaporized feedstock, including diluent which can be present in the feedstock, and conversion products, divided by the cross-sectional area of the reaction zone.

In this invention, the oxygenate is converted to an olefin product, predominantly comprising ethylene and propylene, while flowing through the reaction zone. The GSV may vary at different locations within the reaction zone depending on the total number of moles of gas present and the cross sectional area, temperature, pressure and other relevant reaction parameters at a particular location in the reaction zone. However, it is desirable to maintain a relatively high GSV at all points, particularly the point of contact of the oxygenate feed with the catalyst to maintain a high selectivity to ethylene and propylene.

The gas superficial velocity in the reaction zone should be sufficient to maintain a fluidized catalyst, and provide flow of at least a portion the catalyst from the reaction zone to the recirculation zone. Typically, the gas superficial velocity at the point of contact of feed with total catalyst should be at least about 1.0 meter per second (m/s). Total catalyst in this invention refers to any catalyst that is added to the reaction zone, including fresh catalyst, regenerated catalyst, and catalyst that is recirculated with regeneration. The catalyst can be added at one or more points in the reaction zone. It is desirable, however, to mix the catalyst together and add the mixed catalyst composition to the reaction zone.

The GSV may be increased to more closely approach a hydrodynamic flow regime in the reaction zone that more closely approximates plug flow. As the GSV increases above about 1.0 meter per second, a reduction in axial diffusion, or backmixing, of the gases flowing through the reactor results from a reduction in internal recirculation of solids, which carry gases with them. Minimizing the backmixing of the gases in the reactor increases the selectivity to ethylene and propylene in the oxygenate conversion reaction.

In another embodiment of the invention, the gas superficial velocity is at least about 2.0 m/s at the point of contact with feed and total catalyst. Desirably, the gas superficial velocity is at least about 2.5 m/s. Yet more desirably, the gas superficial velocity is at least about 3.0 m/s. Most desirably, the GSV is at least about 4.0 m/s at the point of contact of total catalyst.

With reference to FIG. 1, an integrated co-catalyst is formed by combining an organic functionality and an inorganic molecular sieve. While not wishing to be limited to a single theory of the mechanism of the formation of the integrated co-catalyst, it is believed that a particularly effective catalyst useful for the conversion of oxygenates to light olefins is the product of contacting a hydrocarbon or oxygenate with an acid binding site 2 of the porous, acidic framework of a small pore molecular sieve catalyst 1. Ideally, the hydrocarbon or oxygenate used to achieve this will have a kinetic diameter less than the pore opening of the molecular sieve. Desirably, co-catalyst formation is carried out at a temperature above about 250° C.

The integrated co-catalyst is believed to consist of an alkylated aromatic ring 3. This alkylated ring integrated with the acidity contributed by the molecular sieve and contained within a small pore framework, is believed to be particularly effective for converting oxygenate feeds into light olefins, particularly ethylene and propylene. The inventors have found that regardless of how the integrated co-catalyst is formed, there is a tendency for the co-catalyst to degrade to an inactive carbonaceous deposit 4 on or within the molecular sieve. This deposit is also referred to herein as coke.

Degradation to a carbonaceous deposit is accelerated by exposure to relatively high temperatures. Thus, upon exposure to relatively high temperatures, the alkylated aromatic is believed to degrade, producing multi-ring dealkylated organic species that are relatively ineffective for converting oxygenate feeds to light olefins.

In general, the process of this invention comprises contacting an oxygenate-containing feedstock with an olefin forming integrated co-catalyst to form an olefin-containing product. After the product is formed, the catalyst and product are separated, and the product is collected. This separation can be accomplished using conventional separation means such as cyclone separators or filters.

After separation, some or all of the catalyst can be sent directly back to the reaction unit, without regeneration, for reacting with additional oxygenate feed. A portion of the separated catalyst can, however, be regenerated if desired. After regeneration, the regenerated catalyst can be combined with the non-regenerated portion of the separated catalyst and recontacted with additional oxygenate feed. The non-regenerated portion of the catalyst is cooled in order to reduce the rate of degradation to coke.

In one embodiment of this invention, coke formation can be inhibited by contacting catalyst with oxygenate as soon as practical following separation of the olefin-containing product from the catalyst. This reduces the amount of time that the integrated co-catalyst is allowed to be exposed to relatively high temperatures. This is turn will reduce the extent of degradation of the organic portion of the integrated co-catalyst. This contact is preferably made between oxygenate and catalyst that is not regenerated. Catalyst that is to be regenerated need not be contacted with oxygenate prior to regeneration, since any product formed or any unreacted oxygenate will likely be oxidized during the regeneration process.

In another embodiment of this invention, coke formation can be inhibited by cooling the catalyst below the average reaction temperature. As defined herein, the average reaction temperature is the average of the reactor inlet temperature and the reactor outlet temperature.

Not all of the catalyst need be cooled. It is preferable, however, to cool the portion of the catalyst that is to be recycled without regeneration. Preferably, the cooled portion of the catalyst will be within a temperature range of about 400 and 470° C., and is at least 10° C. lower than the average reactor temperature. More preferably, the cooled portion of the catalyst is at least 20° C. lower than the average reactor temperature, and most preferably at least 30° C. lower.

In a desirable embodiment of the invention, catalyst is contacted with oxygenate-containing feedstock to form an olefin-containing product. The product is then separated from the catalyst and at least a portion of the catalyst is recycled to the reactor without regeneration for further reaction with oxygenate-containing feed. A portion of the catalyst can be regenerated, if desired, and the regenerated portion is then recycled to the reactor.

Preferably, the portion of the separated catalyst that is not regenerated is cooled, and then combined with the regenerated catalyst portion. Cooling can be accomplished using conventional heat exchange equipment. The cooling medium can also be conventional. Either water or air as the cooling medium is desirable. However, it is preferred to use the feedstock itself so that the exchange of heat will act to preheat the feedstock before it is contacted with catalyst. It is preferred to cool only the non-regenerated catalyst portion. However, the regenerated and non-regenerated catalyst can be combined and then cooled. The feedstock can be injected to the non-regenerated stream before or after cooling, or it can be injected to the combined catalyst before or after cooling.

It is desirable in this invention that a significant portion of the catalyst in the reaction system (i.e., the entire reaction system being the reaction zone, the recirculation zone, which is the zone that reciruclates catalyst without regeneration, and the regeneration zone) be circulated through the recirculation zone; that is, without regeneration. Desirably, the system is operated such that catalyst continually circulates through the reaction zone and recirculation zone at a mass ratio of catalyst in the reaction zone to total amount of catalyst in the reaction and recirculation zone of from about 0.01 to about 0.99:1; preferably from about 0.1 to about 0.90:1; more preferably from about 0.2 to about 0.8:1; and most preferably from about 0.3 to about 0.7:1.

The rate of catalyst recirculated without regeneration to contact the feed to the reaction zone may vary over a wide range. Desirably, the rate of recirculation is from about 1 to about 100 times the total feed rate of oxygenates to the reaction zone. More desirably, the rate of recirculation is from about 10 to about 80 times the total feed rate of oxygenates to the reaction zone, and most desirably from about 10 to about 50 times the total feed rate of oxygenates to the reaction zone.

The catalyst that is used in this invention is one that incorporates a silicoaluminophosphate (SAPO) molecular sieve. The molecular sieve comprises a three-dimensional microporous crystal framework structure of $[SiO_2]$, $[AlO_2]$ and $[PO_2]$ corner sharing tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift $\delta(Si)$ in the range of −88 to −96 ppm and with a combined peak area in that range of at least 20% of the total peak area of all peaks with a chemical shift $\delta(Si)$ in the range of −88 ppm to −115 ppm, where the $\delta(Si)$ chemical shifts refer to external tetramethylsilane (TMS).

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from about 3.5 to 4.2 angstroms. These pore sizes are typical of molecular sieves having 8 membered rings.

In general, silicoaluminophosphate molecular sieves comprise a molecular framework of corner-sharing [SiO$_2$], [AlO$_2$], and [PO$_2$] tetrahedral units. This type of framework is effective in converting various oxygenates into olefin products.

The [PO$_2$] tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The [AlO$_2$] tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The [SiO$_2$] tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an AlPO$_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of MO$_2$, AlO$_2$ and PO$_2$ tetrahedral units. These as manufactured structures (which contain template prior to calcining) can be represented by empirical chemical composition, on an anhydrous basis, as:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means, and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a mean particle size of from about 20 microns to 3,000 microns, more preferably about 30 microns to 200 microns, most preferably about 50 microns to 150 microns.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

The desired aromatic composition of the integrated co-catalyst can be identified by Solid State Nuclear Magnetic Resonance (SSNMR) spectra comprising a peak in the 18–40 ppm region and a peak in the 120–150 ppm region. Preferably, the aromatic composition is selected from the group consisting of alkyl substituted, single ring aromatics. Alternatively, if the intensity of the peak in the 18–40 ppm region is negligible, a single peak near 128 ppm also indicates a useful material of this invention, as this indicates the presence of benzene. Benzene also has the desired effect on catalytic activity, as it rapidly reacts with the oxygenate to make alkylated single ring aromatics.

Preferably the integrated hydrocarbon co-catalyst which may be a single ring aromatic within the silicoaluminophosphate molecular sieve or catalyst containing the silicoaluminophosphate molecular sieve will exhibit a ratio of the intensity of the peak in the 18–40 ppm region to the intensity of the peak in the 120–150 ppm region of not greater than 1.0. More preferably, the integrated hydrocarbon co-catalyst which may be a single ring aromatic within the silicoaluminophosphate molecular sieve or catalyst containing the silicoaluminophosphate molecular sieve will exhibit a ratio of the intensity of the peak in the 18–40 ppm region to the intensity of the peak in the 120–150 ppm region of between about 0.15 and about 0.7.

It is desirable that the integrated hydrocarbon co-catalyst be present within the porous structure of the silicoaluminophosphate molecular sieve in an amount effective to enhance the conversion of oxygenate feed to olefin product, particularly at a concentration effective to enhance selectivity to ethylene and/or propylene. The integrated hydrocarbon co-catalyst can be part of a hydrocarbon composition within the porous structure of the silicoaluminophosphate molecular sieve. Preferably, the hydrocarbon composition within the porous structure is a single ring aromatic. It is also desirable that the co-catalyst be present at about 0.1–23 wt. % based on the total weight of the silicoaluminophosphate molecular sieve.

Optionally, the organic portion of the integrated co-catalyst may be formed prior to contacting with the oxygenate feed. This pretreatment may be carried out in accordance with U.S application Ser. No. 09/593,620, incorporated herein by reference.

Regardless of whether any pretreatment is used to form the co-catalyst, the activity and selectivity of the catalyst will be impaired if the co-catalyst is converted to coke. In general, coke forming within the pores of the molecular sieve tends to deactivate the catalyst. Coke formation in general can be inhibited by maintaining contact between active catalytic sites on and/or within the molecular sieve and oxygenate molecules at appropriate olefin conversion conditions. In addition, coke formation can be inhibited by selective cooling of catalyst.

In this invention, a feed containing the oxygenate, and optionally a diluent or a hydrocarbon added separately or mixed with the oxygenate, is contacted with a catalyst containing a SAPO molecular sieve in a reaction zone or volume. The volume in which such contact takes place is herein termed the "reactor," which may be a part of a "reactor apparatus" or "reaction system." Another part of the reaction system may be a "regenerator," which comprises a volume wherein carbonaceous deposits (or coke) on the catalyst resulting from the olefin conversion reaction are removed by contacting the catalyst with regeneration medium.

Another part of the reactor system is a device for cooling the integrated co-catalyst after it is separated from the olefin product stream and prior to re-introduction to the reaction system. In various embodiments of this invention, a portion of the catalyst will be directed to a regenerator. In the regenerator part or all of the coke and other hydrocarbons remaining on the catalyst will be removed by various means. These means include contacting the catalyst with oxygen containing gas, steam, hydrogen or other suitable means. Alternatively, the catalyst may be regenerated in the reaction system after the oxygenated feed has been removed. It is generally preferable to maintain a certain average level of carbonaceous deposits and organic portion of the integrated co-catalyst.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are Ghydrocarbon compositions which are converted to another chemical arrangement when contacted with molecular sieve catalyst. These hydrocarbons can include wolefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

According to a preferred embodiment of this invention, it is expected that coke formation will be inhibited. This does not mean that coke formation will be eliminated, but that the tendency to form coke will be reduced, i.e., that total coke formation should be reduced. Even at reduced coke formation, it is desirable to remove at least some of the coke level by regenerating at least a portion of the catalyst and returning the regenerated catalyst back to the reaction unit. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

The conversion of oxygenates to produce light olefins may be carried out in a variety of catalytic reactors. Reactor types include fixed bed reactors, fluid bed reactors, and concurrent riser reactors as described in "Free Fall Reactor,"

*Fluidization Engineering,* D. Kunii and 0. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor", *Fluidization and Fluid-Particle Systems,* pages 48–59, F. A. Zenz and D. F. Othlno, Reinhold Publishing Corp., NY 1960, the detailed descriptions of which are also expressly incorporated herein by reference.

Any standard reactor system can be used, including fixed bed, fluid bed or moving bed systems. In such a reactor an oxygenate feedstock can be contacted with a molecular sieve catalyst at a WHSV of at least about 1 $hr^{-1}$, preferably ranging from about 20 $hr^{-1}$ to about 1000 $hr^{-1}$, and most preferably in the range of from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

In one embodiment of this invention, the reaction conditions for making olefins from an oxygenate feedstock in the reaction zone comprise a WHSV of at least about 20 $hr^{-1}$ and a Temperature Corrected Normalized Methane Selectivity (TCNMS) of less than about 0.016. As used herein, TCNMS is defined as the Normalized Methane Selectivity (NMS) when the temperature is less than 400° C. The NMS is defined as the methane product yield divided by the ethylene product yield wherein each yield is measured on or is converted to a weight % basis. When the temperature is 400° C. or greater, the TCNMS is defined by the following equation, in which T is the average temperature within the reactor in ° C.:

$$TCNMS = \frac{NMS}{1 + (((T-400)/400) \times 14.84)}.$$

It is desirable in this invention that oxygenate conversion, referring to the oxygenate species per se and not including any hydrocarbon co-feed, should be maintained sufficiently high to avoid the need for commercially unacceptable levels of oxygenate feedstock recycling. While 100% oxygenate conversion is desired for the purpose of potentially completely avoiding oxygenate feedstock recycle, a reduction in undesirable byproducts is observed frequently when the conversion is about 99% or less, and incremental economic improvements may occur when the conversion is about 98% or less, further to about 96% or less, and still further to about 94% or less. Since recycling up to as much as about 50% of the feed can be commercially acceptable, conversion rates from about 50% to about 98% are desired. Oxygenate conversion rates may be maintained in the range of about 50% to about 99% using a number of methods familiar to persons of ordinary skill in the art. Examples include, but are not necessarily limited to, adjusting one or more of the following: reaction temperature; pressure; flow rate (weight hourly space velocity and/or gas superficial velocity); catalyst recirculation rate; reactor apparatus configuration; reactor configuration; feed composition; amount of liquid feed relative to vapor feed; amount of recirculated catalyst; degree of catalyst regeneration; and other parameters which affect the conversion.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

In a preferred embodiment of the continuous operation, only a portion of the catalyst is removed from the reactor and sent to the regenerator to remove coke deposits, which may have accumulated during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, at least a part of the coke deposits are removed from the catalyst during the regeneration process, forming a regenerated catalyst. The regenerated catalyst is then returned to the reactor for further contact with feed. Typical regeneration temperatures are in the range of 250–700° C., desirably in the range of 350–700° C. Preferably, regeneration is carried out at a temperature range of 450–700° C.

It is desirable to strip at least some of the volatile organic components that may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature that is from about 200° C. higher to about 200° C. lower than the temperature of the catalyst withdrawn from the reactor. More desirably, it is cooled to a temperature ranging from about 10 to about 200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred that the catalyst within the reactor has an average level of integrated co-catalyst material effective for selectivity to ethylene and/or propylene. Preferably, the co-catalyst material will comprise a substantial amount of the co-catalyst composition such that a high level of selectivity and activity can be maintained. In a commercial scale operational system, however, it may be difficult to distinguish between carbonaceous co-catalyst composition and carbonaceous coke. Therefore, it is desirable to maintain the catalyst within the reactor at an average carbonaceous content of from about 2 wt. % to about 30 wt. %, more preferably from about 2 wt. % to about 20 wt. %. In order to maintain this average level of carbonaceous material on catalyst, it may be necessary to regenerate a portion of the catalyst. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

At any given instant in time, some of the catalyst in the reactor apparatus may be fresh, some regenerated, and some coked or partially coked as a result of having not yet been regenerated. Therefore, various portions of the catalyst in the reactor apparatus may have been feedstock exposed for different periods of time. Since the rate at which oxygenate feedstock and catalyst flows to the reactor apparatus can vary, the amount of feed to which various portions of the catalyst have been exposed can also vary. To account for this variation, the "average catalyst feedstock exposure index (ACFE index)" is used to quantitatively define the extent to which the entire catalyst in the reactor apparatus has been feedstock exposed.

As used herein, ACFE index is the total weight of oxygenate feedstock plus optional hydrocarbon feed sent to the reactor apparatus divided by the total weight of fresh and regenerated molecular sieve (i.e., excluding binder, inerts, etc., of the catalyst composition) sent to the reaction zone, both total weights measured over the same period of time. The measurement should be made over an equivalent time interval, and the time interval should be long enough to smooth out fluctuations in catalyst or feedstock rates according to the reactor apparatus and regeneration process step selected to allow the system to be viewed as essentially continuous. In the case of reactor systems with periodic regenerations, this can range from hours up to days or longer. In the case of reactor systems with substantially constant regeneration, minutes or hours may be sufficient.

In one embodiment of this invention, an oxygenate feedstock, and optionally a hydrocarbon feed, either separately or mixed with the oxygenate, is contacted with a catalyst containing a SAPO molecular sieve at process conditions effective to produce olefins in a reactor apparatus where the catalyst has an ACFE index of at least about 1.0, preferably at least about 1.5, more preferably at least about 2.0. An ACFE index in the range of about 1.0 to about 20 is effective, with a range of about 1.5 to about 15 being desirable. A range of about 2.0 to about 12 is particularly preferred.

Figure 2:
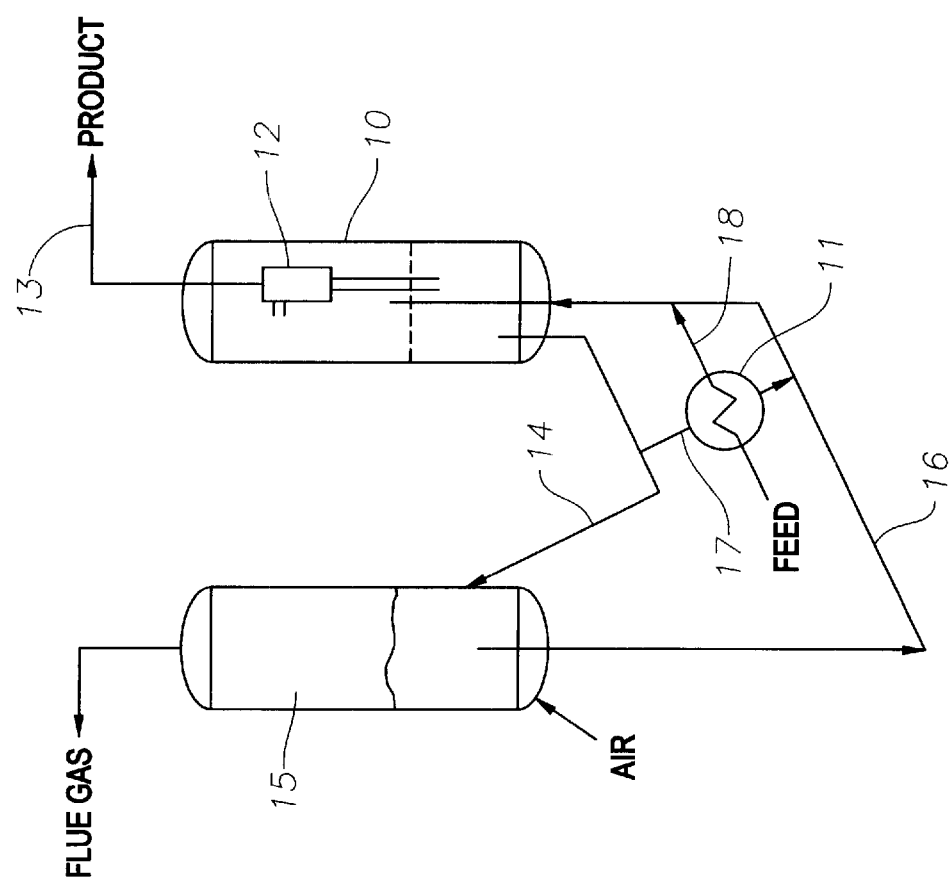
FIG. 2 is a schematic of a fluid bed oxygenate conversion apparatus including a means for catalyst cooling.

A preferred embodiment of the reaction system of this invention is shown in FIG. 2, with the reaction being carried out in a fluidized bed reactor 10. Oxygenate feed is introduced into the system through a heat exchanger 11. The heat exchanger 11 exchanges heat between catalyst exiting the reactor 10 along lines 14 and 17 and the feed entering the reactor along lines 18 and 16. This exchange acts to cool the catalyst to inhibit coke formation, as well as to heat the feed.

After the feed is heated, it comes into actual contact with the catalyst at the junction of lines 18 and 16. Upon contact, the feed is converted into product. This conversion is continued as the mix of catalyst and feed enters into reactor 10, and is finally quenched through separation of catalyst from any unreacted feed. Even if all the feed has been converted to product, there is a tendency for smaller product molecules to continue reaction as long as the molecules are in contact with the catalyst. For example, ethylene and propylene can form oligomers, and the reaction can continue to form coke, which will act to deactivate the catalyst.

Any unreacted feed and/or product formed is separated from the catalyst by an appropriate filtering or separation means 12. Any conventional means can be used. Cyclone separators are preferred. It is preferable that at least a coke inhibiting amount of oxygenate remain in contact with the catalyst until separation is effectively accomplished. Following separation, product is removed through line 13. The catalyst preferably flows downward from separator 12, forming a dense, fluidized bed. The catalyst is then removed through line 14 and either passed through the heat exchanger 11 along line 17 or carried to the catalyst regenerator 15.

Under conditions where reactor 10 is operated to inhibit coke formation, coke formation is nevertheless likely to occur. Since significant coke formation will deactivate the catalyst, a portion of the catalyst is sent to a regenerator 15, where oxidation of the coke takes place. Conventional regeneration means can be used. Once oxidation is effectively complete, the regenerated catalyst is returned to the reactor 10 along line 16.

Figure 3:
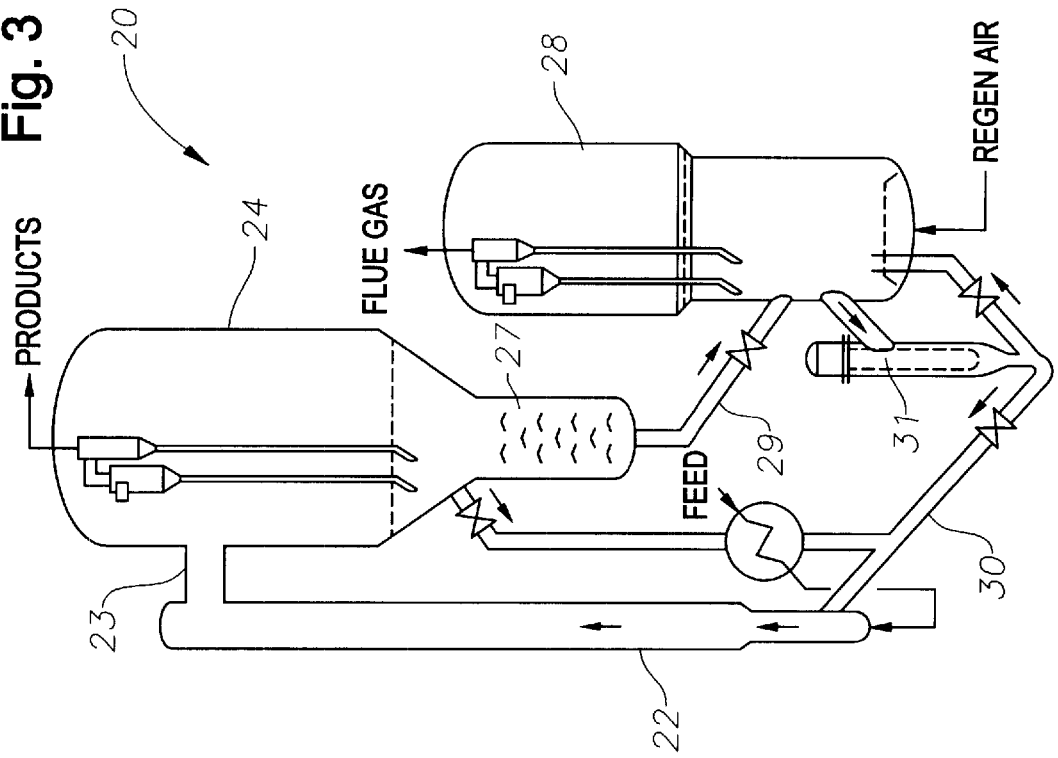
FIG. 3 is a schematic of riser reactor conversion apparatus including means for catalyst cooling.

Another embodiment of the reaction system of this invention is shown in FIG. 3, with the reaction being carried out in a riser reactor system 20. In this embodiment, oxygenate feed is used to cool non-regenerated catalyst to inhibit coke formation. The cooled catalyst is mixed with regenerated catalyst and is input to an external riser section 22 of the riser reactor system. An inert gas and/or steam may be used to dilute the oxygenate, lift the catalyst stream, and keep pressure instrument lines clear of catalyst. This inert gas and/or steam mixes with the feed and catalyst in the riser section. Effluent from the external riser section 22, containing products, catalyst, diluents, and preferably unconverted feed, is sent through a line 23 to a separate disengaging zone 24. In the disengaging zone 24, catalyst is separated from the gaseous materials by conventional means, such as gravity settling, filters, and/or cyclone separators.

A portion of the catalyst is sent from disengaging zone 24 to a stripping zone 27, where steam or other inert gas is injected (not shown) to recover adsorbed hydrocarbons from the catalyst. Stripped catalyst is then sent to a regenerator 28 through a line 29. The catalyst in the regenerator 28 is contacted with a regeneration medium, preferably a gas comprising oxygen.

The regenerated catalyst is sent to the riser section 22 through a line 30 to continue the reaction process. The regenerated catalyst can be lifted into the riser section by means of an inert gas, steam, or oxygenate vapor (not shown). The process should repeat itself in a continuous or semi-continuous manner. If desired, the temperature in the regenerator 28 can be cooled by recycling the regenerated catalyst through a catalyst cooler 31.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst.

Product that is initially removed from the disengaging zone is desirably high in prime olefin (i.e. ethylene and propylene) content. In an appropriately operating system, ethylene and propylene can be separated by conventional fractionation processes, preferably using a single fractionation tower, and recovered each is recovered for further processing. Preferably, the product from the disengaging zone will contain greater than 70 wt. % ethylene and propylene, more preferably at least 75 wt. %, and most preferably at least 80 wt. %. It is also preferred that ethylene and propylene be present at an ethylene to propylene weight ratio of at least 0.8:1, preferably 1.0:1, and most preferably at least 1.5:1.

In another preferred embodiment, the product that is initially removed from the disengaging zone is desirably low in paraffin components. Preferably, paraffin content is sufficiently low such that separation of olefins and paraffins of the same carbon number are not necessary. This will greatly reduce the capital cost as well as the cost of operation. For example, once ethylene and propylene have been separated from the initial product by conventional means into ethylene and propylene fractions, there is no need to further purify either the ethylene or propylene fraction of paraffin content. This avoids using additional separation equipment such as conventional distillation means (e.g., superfractionaters) to remove undesirable quantities of ethane from the ethylene fraction or propane from the propylene fraction. Such fractions can then be sent directly to additional reaction units for further reacting the ethylene or propylene into derivative products. It is preferred that the ethylene fraction of such process comprise at least 85 wt. % ethylene, preferably at least 90 wt. %, most preferably at least 95 wt. %. It is also preferred that the propylene fraction of such process comprise at least 85 wt. % propylene, preferably at least 90 wt. %, most preferably at least 95 wt. %.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

General Experimental Procedure

Catalyst Activity Index

The conversion of methanol was used as a means of determining the activity of catalyst in the presence of contained Hydrocarbons, subsequently referred to as "coke". A master sample of SAPO-34 was preloaded with 8.24% coke to simulate a combination catalyst-coke composite (CCC). The activity of this catalyst was determined by placing 10.36 mg of the CCC in a 4 mm diameter stainless steel reactor. The CCC was diluted with 68.5 mg of inert SiC to facilitate flow and to reduce the effect of the exothermic release of heat on the reactor conditions. Methanol vapor was generated by vaporizing liquid methanol fed to the reactor at a rate of 43.7 ml/min. The outlet pressure of the reactor was maintained at 25 psig (273 kPa) and the temperature was varied by means of an electric furnace surrounding the reactor tube. The reference temperature was 450° C. Gas phase products were collected from the effluent stream in a series of sample collection loops. The samples thus collected were successively injected into an HP 6890 gas chromatograph equipped with a Flame Ionization Detector. Methanol conversion was calculated on a water free basis as:

$$X(conv) = \frac{\text{wt (MeOH + DME)}}{\text{wt MeOH + wt DME + wt HC}} \quad (1)$$

where, MeOH is methanol; DME is dimethyl ether (considered to be equivalent to unreacted methanol).

HC=hydrocarbons; gas phase products of the reactions, comprising ethylene, propylene, other olefins and aliphatics.

A pseudo—first order rate constant was calculated from the calculated conversion extent (1) by:

$$K = \ln(1-x) * WHSV \times (3600 \text{ sec/hr}) \quad (2)$$

where $K$ = pseudo – 1st order rate constant, $\text{sec}^{-1}$ $x$ = conversion ratio (1)

$WHSV$ = weight hourly space velocity $$= \frac{\text{MeOH feed/hr (grams)}}{\text{catalyst in reactor (grams)}}$$

$1/3600$=conversion factor of hour to secs

In experiments requiring measurement of the effect of placing the CCC in a heater, the CCC was placed in the reactor as described above and heated to various temperatures for various times. After sufficient heating of the catalyst, the reactor was either cooled or heated as appropriate, to 450° C. for testing of the catalyst activity.

COMPARATIVE EXAMPLE 10.36 mg of calcined CCC, as described above, was mixed with 68.15 mg of SiC and placed in a 4 mm i.d. reactor. Vaporized methanol was passed through the catalyst bed at 43.7 ml/min. The WHSV was calculated to be 200 hr$^{-1}$. The reactor was maintained at 450° C. and the pressure was maintained at 25 psig (273 kPa). Three samples were taken and analyzed via gas chromatograph (GC) and the 1st order rate constants were calculated. The results are shown in Table 1.

EXAMPLE 1

The procedure in the Comparative Example was repeated. However, the CCC was heated at 450° C. for 3 hrs. The activity results are listed in Table 1 as Example 1.

EXAMPLES 2, 3, 4, 5, 6

The Comparative Example was repeated, except that the CCC was held as follows:

450° C.—for 6 hours (Example 2)
550° C.—for 0.5 hrs (Example 3)
550° C.—for 3.0 hrs (Example 4)
650° C.—for 0.5 hrs (Example 5)
650° C.—for 3.0 hrs (Example 6)

Results are listed in Table 1.

TABLE 1

Effect of Thermal Aging on Activity

|  | Aging Temperature [° C.] | Aging Time [hr]. | Rate Constant[a] [l/s] |
|---|---|---|---|
| Comparative | 450 | (no aging) | 113 |
| Example 1 | 450 | 3.0 | 110 |
| Example 2 | 450 | 6.0 | 94 |
| Example 3 | 550 | 0.5 | 101 |
| Example 4 | 550 | 3.0 | 58 |
| Example 5 | 650 | 0.5 | 39 |
| Example 6 | 650 | 3.0 | 40 |

[a]Based on clean, dry SAPO-34 sieve at 450° C., 25 psig MeOH.

Table 1 shows, inter alia, that a loss of 11% was observed at 550° C. at an exposure time of 30 minutes and 49% at three hours cumulative exposure time.

From the results listed in Table 1 it was found that the loss in activity, as represented pseudo first-order rate constant, could be estimated by the following formula:

$$k_D = K_O \exp\left(-\frac{E_a}{RT}\right) \quad (3)$$

where $K_o$ is the pre-exponential factor; $E_a$ is the Arrhenius activation energy for the deactivation process; R is the universal gas constant; and T is the average reaction temperature in ° K. The estimates were then used to calculate the relative rate constant at various combinations of time and temperature The calculated relative rate constant values are shown in Table 2.

This relative rate constant is defined as:

$$Rd/\text{Rate Constant} = KD/Kref \times 100\% \quad (4)$$

Where Kref is the reference rate constant under there conditions of the comparative, 113 sec$^{-1}$.

Equation (4) was used to calculated expected relative rate constants at several intermediate exposure times/temperatures and the results of these combinations are shown in Table 2. It is obvious to one skilled in the art that other combinations could all be calculated.

TABLE 2

Estimated Effect of Thermal Aging on Activity[a]

| Aging Temperature [° C.] | Aging Time [hr.] | Relative Rate Constant[b] [%] |
|---|---|---|
| 425 | 3.0 | 97 |
| 425 | 6.0 | 94 |
| 450 | (no aging) | 100 |
| 450 | 3.0 | 94 |
| 450 | 6.0 | 88 |
| 475 | 3.0 | 88 |
| 475 | 6.0 | 78 |
| 500 | 3.0 | 79 |
| 500 | 6.0 | 63 |
| 525 | 3.0 | 66 |
| 525 | 6.0 | 44 |

[a]Parameters for Eq. 2: In $K_0$ 11.926 and $E_a$ = 119 kJ/mol
[b]Rate constant as percentage of non-aged rate constant (i.e. $A_0$ = 100)

Other relative rate constants can be calculated by equation (3).

Table 2 shows that an activity loss of 21% can be expected with aging at 500° C. for 3 hours and up to 37% loss can be expected at 6 hours. Reducing the the temperature of the catalyst return stream to 475° C. would reduce these activity losses at the same exposure times to 12% and 22%, respectively.

Having now fully described this invention, it will be appreciated by those skilled in the art that the invention can be performed within a wide range of parameters within what is claimed, without departing from the spirit and scope of the invention.

What is claimed is:

1. A method of inhibiting catalyst coke formation in the manufacture of an olefin-containing product, comprising:
   contacting an oxygenate-containing feedstock with a silicoaluminophosphate molecular sieve catalyst at an average reactor temperature effective to form the olefin-containing product;
   separating the olefin-containing product from the catalyst;
   cooling at least a portion of the separated catalyst below the average reactor temperature; and
   contacting the cooled portion of the catalyst with additional oxygenate-containing feedstock at a gas superficial velocity of at least 1.0 meters per second, wherein the cooled portion of the catalyst has not been regenerated prior to contact with the additional oxygenate-containing feedstock.

2. The method of claim 1, wherein the average reactor temperature is from about 350° C. to about 550° C.

3. The method of claim 1, wherein the cooled portion of the catalyst is at a temperature of from about 300° C. to about 525° C., and is lower than the average reactor temperature.

4. The method of claim 2, wherein the cooled portion of the catalyst is at least 10° C. lower than the average reactor temperature.

5. The method of claim 4, wherein the cooled portion of the catalyst is at least 20° C. lower than the average reactor temperature.

6. The method of claim 5, wherein the cooled portion of the catalyst is at least 30° C. lower than the average reactor temperature.

7. The method of claim 1, wherein a portion of the separated catalyst is regenerated, and the regenerated catalyst is combined with the cooled portion of the catalyst prior to contacting with the additional oxygenate-containing feedstock.

8. The method of claim 1, wherein a portion of the separated catalyst is regenerated, and the regenerated catalyst is combined with the cooled portion of the catalyst after the cooled portion of the catalyst has been contacted with the additional oxygenate-containing feedstock.

9. The method of claim 1, further comprising collecting the separated olefin-containing product and separating compounds contained therein to recover an olefin product containing at least 85 wt. % ethylene.

10. The method of claim 9, further comprising converting the product containing at least 85 wt. % ethylene to polyethylene.

11. The method of claim 1, further comprising collecting the separated olefin-containing product and separating compounds contained therein to recover an olefin product containing at least 85 wt. % propylene.

12. The method of claim 11, further comprising converting the product containing at least 85 wt. % propylene to polypropylene.

13. The method of claim 8, wherein the regenerated catalyst has an average coke content of less than 2 wt. %.

14. The method of claim 7 or 8, wherein the combination of separated and regenerated catalyst has an average coke content of between 2 wt. % and 30 wt. %.

15. The method of claim 1, wherein the oxygenate-containing feedstock comprises at least one compound selected from the group consisting of methanol, ethanol, n-propanol, isopropanol, $C_4$–$C_{20}$ alcohols, methyl ethyl ether, dimethyl ether, diethyl ether, di-isopropyl ether, formaldehyde, dimethyl carbonate, dimethyl ketone, acetic acid, and mixtures thereof.

16. The method of claim 15, wherein the oxygenate-containing feedstock comprises methanol or dimethyl ether.

17. The method of claim 16, wherein the oxygenate-containing feedstock comprises methanol.

18. The method of claim 1, wherein the molecular sieve is a silicoaluminophosphate molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, mixtures thereof, and intergrowths thereof.

19. The method of claim 18, wherein the silicoaluminophosphate molecular sieve is SAPO-34 or SAPO-18.

20. The method of claim 19, wherein the silicoaluminophosphate molecular sieve is SAPO-34.

21. The method of claim 1, wherein the oxygenate-containing feedstock is contacted with the silicoaluminophosphate catalyst at a temperature ranging from 200° C. to 700° C.

22. The method of claim 1, wherein the oxygenate-containing feedstock is contacted with the silicoaluminophosphate catalyst in a reactor at a gas superficial velocity of at least 2 meters per second.

23. A method of inhibiting catalyst coke formation in the manufacture of an olefin-containing product, comprising:
    contacting an oxygenate-containing feedstock with a silicoaluminophosphate molecular sieve catalyst at an average reactor temperature of from 350 to 550° C. to form the olefin-containing product;
    separating the olefin-containing product from the catalyst;
    regenerating a first portion of the separated catalyst;
    cooling a second portion of the separated catalyst below the average reactor temperature;
    combining the regenerated and cooled catalyst portions; and
    contacting the combined catalyst portions with additional oxygenate containing feedstock.

24. The method of claim 23, wherein the cooled portion of the catalyst is at a temperature of from 300° C. to 525° C., and is lower than the average reactor temperature.

25. The method of claim 24, wherein the cooled portion of the catalyst is at least 10° C. lower than the average reactor temperature.

26. The method of claim 25, wherein the cooled portion of the catalyst is at least 20° C. lower than the average reactor temperature.

27. The method of claim 26, wherein the cooled portion of the catalyst is at least 30° C. lower than the average reactor temperature.

28. The method of claim 23, further comprising collecting the separated olefin-containing product and separating compounds contained therein to recover an olefin product containing at least 85 wt. % ethylene.

29. The method of claim 28, further comprising converting the product containing at least 85 wt. % ethylene to polyethylene.

30. The method of claim 23, further comprising collecting the separated olefin-containing product and separating compounds contained therein to recover an olefin product containing at least 85 wt. % propylene.

31. The method of claim 30, further comprising converting the product containing at least 85 wt. % propylene to polypropylene.

32. The method of claim 23, wherein the catalyst separated from the olefin-containing product has an average coke content of at least 2 wt. %.

33. The method of claim 23, wherein the regenerated catalyst has an average coke content of less than 2 wt. %.

34. The method of claim 23, wherein the combination of separated and regenerated catalyst has an average coke content ranging from 2 wt. % to 30 wt. %.

35. The method of claim 23, wherein the oxygenate-containing feedstock comprises at least one compound selected from the group consisting of methanol, ethanol, n-propanol, isopropanol, $C_4$–$C_{20}$ alcohols, methyl ethyl ether, dimethyl ether, diethyl ether, di-isopropyl ether, formaldehyde, dimethyl carbonate, dimethyl ketone, acetic acid, and mixtures thereof.

36. The method of claim 35, wherein the oxygenate-containing feedstock comprises methanol or dimethyl ether.

37. The method of claim 36, wherein the oxygenate-containing feedstock comprises methanol.

38. The method of claim 23, wherein the molecular sieve is a silicoaluminophosphate molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, mixtures thereof, and intergrowths thereof.

39. The method of claim 38, wherein the silicoaluminophosphate molecular sieve is SAPO-34 or SAPO-18.

40. The method of claim 39, wherein the silicoaluminophosphate molecular sieve is SAPO-34.

41. The method of claim 23, wherein the oxygenate-containing feedstock is contacted with the silicoaluminophosphate catalyst at a temperature ranging from 200° C. to 700° C.

42. The method of claim 23, wherein the oxygenate-containing feedstock is contacted with the silicoaluminophosphate catalyst in a reactor at a gas superficial velocity of at least 2.0 meters per second.

43. A method of inhibiting catalyst coke formation in the manufacture of an olefin-containing product, comprising:
    contacting an oxygenate-containing feedstock with a silicoaluminophosphate molecular sieve catalyst at an average reactor temperature of from 350° C. to 550° C.;
    separating the olefin-containing product from the catalyst;
    cooling at least a portion of the separated catalyst to a temperature of from 300° C. to 325° C., and below the average reactor temperature; and
    contacting the cooled portion of the catalyst with additional oxygenate-containing, wherein the cooled portion of the catalyst has not been regenerated prior to contact with the additional oxygenate-containing feedstock.

44. The method of claim 43, wherein the feedstock and catalyst are contacted at a gas superficial velocity of at least 1.0 meters per second.

45. The method of claim 43, wherein the cooled portion of the catalyst is at least 10° C. lower than the average reactor temperature.

46. The method of claim 45, wherein the cooled portion of the catalyst is at least 20° C. lower than the average reactor temperature.

47. The method of claim 46, wherein the cooled portion of the catalyst is at least 30° C. lower than the average reactor temperature.

48. The method of claim 43, wherein a portion of the separated catalyst is regenerated, and the regenerated catalyst is combined with the cooled portion of the catalyst prior to contacting with the additional oxygenate-containing feedstock.

* * * * *